United States Patent [19]

Gaudreault et al.

[11] Patent Number: 5,140,013

[45] Date of Patent: Aug. 18, 1992

[54] MALEIC ANHYDRIDE DERIVATIVES USED AS CONJUGATION AGENTS OF ANTI-TUMOR AGENTS ON DESIRED CARRIERS

[75] Inventors: René C. Gaudreault, Bernière; Colette Mongrain, Ste-Thècle, both of Canada

[73] Assignee: Universite Laval, Quebec, Canada

[21] Appl. No.: 442,130

[22] Filed: Nov. 28, 1989

[51] Int. Cl.$^5$ .................. A61K 37/04; A61K 39/44; C07K 17/02
[52] U.S. Cl. ......................... 514/21; 514/12; 514/8; 530/363; 530/327; 530/345; 530/391.9; 530/395; 530/399; 530/405; 530/406; 530/408; 530/409; 424/85.91
[58] Field of Search ............... 530/363, 389, 390, 391, 530/408, 409, 405, 406, 327, 345, 391.9, 395, 399, 807, 816; 514/12, 21, 8; 424/85.91

[56] References Cited

U.S. PATENT DOCUMENTS

| | | | |
|---|---|---|---|
| 4,569,789 | 2/1986 | Blattler et al. | 424/85.91 |
| 4,631,190 | 12/1986 | Shen et al. | 424/85.91 |
| 4,764,363 | 8/1988 | Blattler et al. | 424/85.91 |
| 4,997,913 | 5/1991 | Hellstrom et al. | 530/389 |

FOREIGN PATENT DOCUMENTS 2756604 6/1978 Fed. Rep. of Germany .

OTHER PUBLICATIONS

Baurain (1977)[CA 88: 89983k, p. 549, 1978].
Baurain (1978) [CA 90: 72437d, p. 541, 1979].
Blair et al. (1983) J. Immunol. Methods 59: 129–143.
Fujiwara et al. (1981) J. Immunol. Methods 45: 195–203.

Primary Examiner—Christine Nucker
Assistant Examiner—Kay K. Kim
Attorney, Agent, or Firm—Dressler, Goldsmith, Shore, Sutker & Milnamow, Ltd.

[57] ABSTRACT

The present invention relates to anti-tumor-conjugation agent-protein compounds of the general formula I:

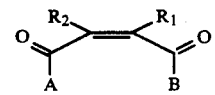

wherein, $R_1$ and $R_2$ are each independently selected from hydrogen atom, $C_{1-4}$alkyl, $C_{1-4}$alkoxy, $C_{1-6}$carboxyalkyl, phenyl, or phenyl substituted by at least one of hydroxy, halogen, lower alkyl, lower alkoxy, or nitro, with the proviso that $R_1$ and $R_2$ cannot be simultaneously a hydrogen, and when one of $R_1$ or $R_2$ is a hydrogen, the other one cannot be —$CH_2COOH$;

A is the residue of an anti-tumor agent containing at least one amino group available to form an amide bound; and B is a free $\epsilon$-lysine containing residue selected from a peptide or a protein.

6 Claims, 2 Drawing Sheets

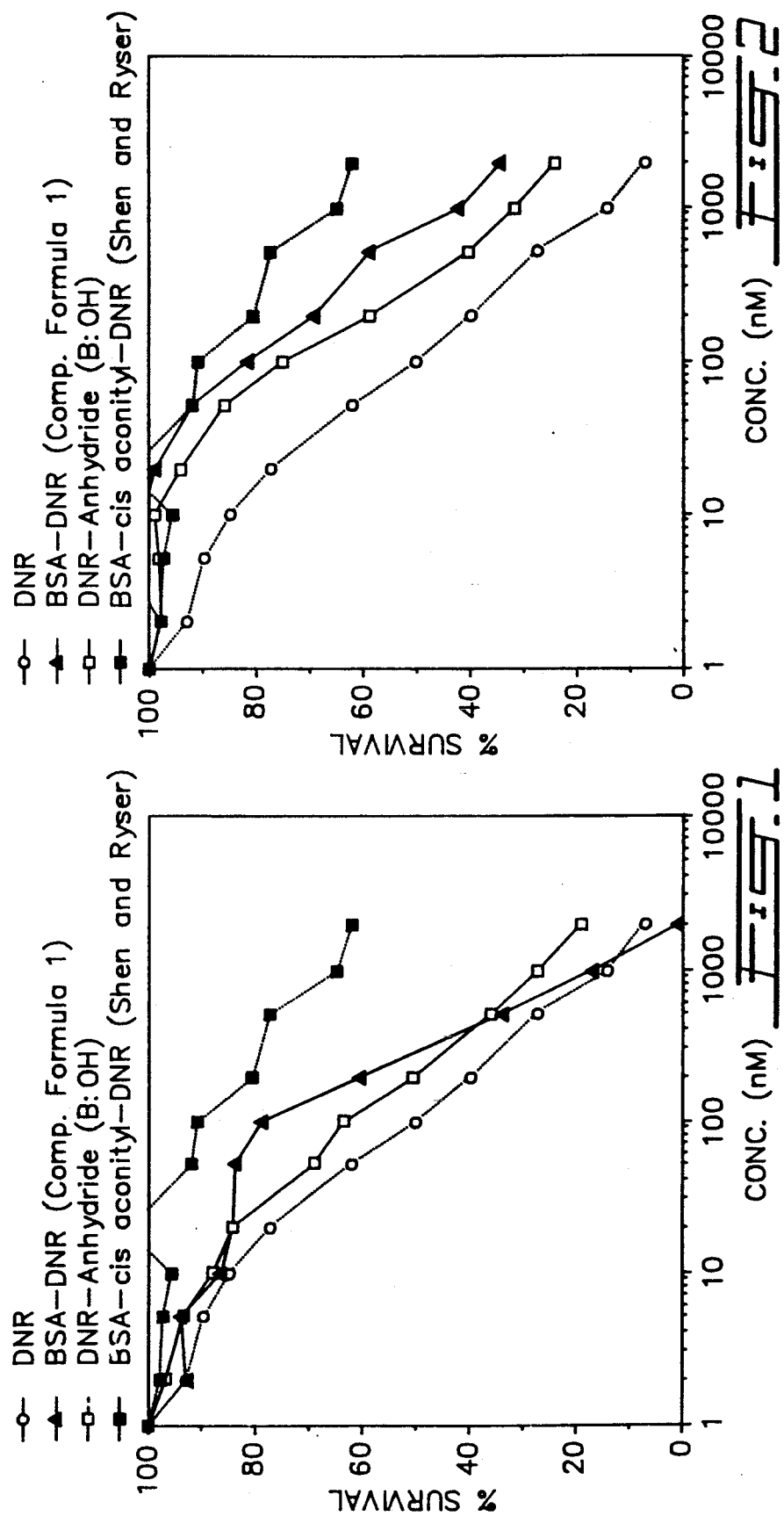

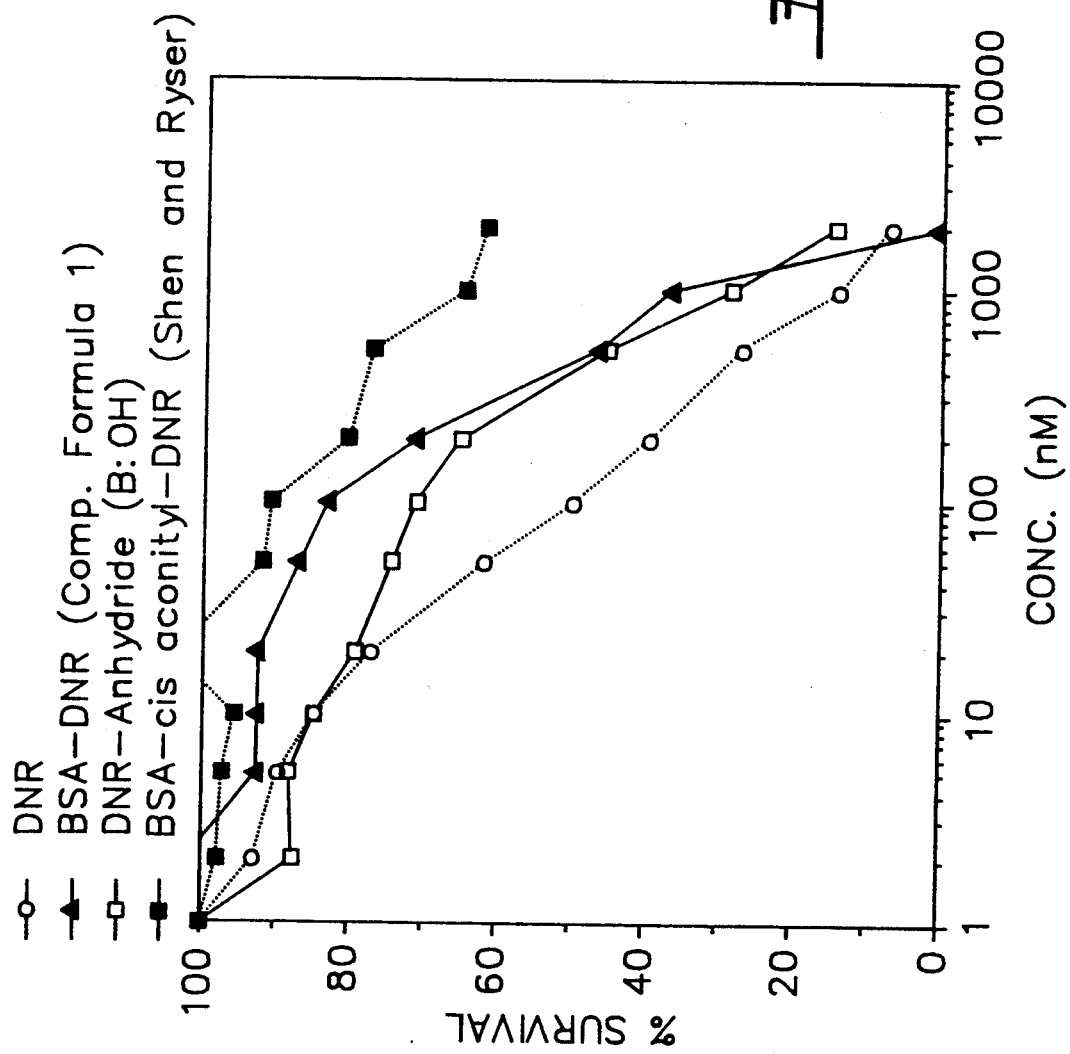

MALEIC ANHYDRIDE DERIVATIVES USED AS CONJUGATION AGENTS OF ANTI-TUMOR AGENTS ON DESIRED CARRIERS

BACKGROUND OF THE INVENTION

Chemotherapeutic agents currently used for anti-tumour therapy are selected for their toxicity towards rapidly proliferating cells. Most of them cause undersirable systemic effects such as cardiac or renal toxicity, marrow aplasia, alopecia, nausea and vomiting. During the last few years, many authors have tried to eliminate these side effects by increasing the availability of the drug to the tumor site. Enzymes, radioisotopes, DNA, toxins, various macromolcules, and antibodies against fibrin or against tumour-specific surface antigens are bound to drugs in an attempt to increase the selectivity of the chemotherapeutic agents, or to decrease their toxic effects on normal cells (Rubens R. D., Lancet, 1974, 1, pp. 498–499; Gregoriadis G. et al., Res. Commun. Chem. Pathol. Pharm., 1975, 10, (2), 351–362).

The targeting of drugs to a tumour by antibodies to surface antigens may have considerable implications by increasing the therapeutic index.

It is recognized that the ideal antineoplastic drug would destroy cancer cells without adverse effects or toxicities on normal cells, but no such drug exists yet. However, despite the narrow therapeutic index of many drugs, treatment and even cure are possible in some patients.

Dactinomycin, doxorubicin and daunorubicin are all given rapidly intravenously and all cause tissue necrosis if extravasation occurs. When doxorubicin and daunorubicin are given rapidly intravenously, there is rapid dispersement throughout tissues and plasma. Their biological half-life is 30 min, with detectable plasma levels of doxorubicin up to 15 h. Both doxorubicin and daunorubicin are extensively metabolized by the liver, yielding active and inactive metabolites.

Daunorubicin is effective in treating acute leukemia. On the other hand, doxorubicin is one of the most active antineoplastics ever identified. In fact it is used to treat acute leukemia, Hodgkin's disease and non-Hodgkin's lymphomas, small cell and non-small cell lung cancer, cancers of the breast, ovaries, stomach, thyroid, and bladder, osteogenic and soft tissue sarcomas, and malignant melanoma. The side effects include nausea, vomiting, alopecia, myelosuppression, and dose-dependent cardiotoxicity ($>550$ mg/m$^2$).

The effectiveness of most anti-tumor agents is greatly reduced because of the nature of the illness and the high toxicity of those active products. It is believed that the problem of high toxicity of the anti-tumor agents can be circumvented by activating the anti-tumor agents with a chemical entity, thereby reducing the toxicity of these drugs without decreasing their effectiveness.

In U.S. Pat. No. 4,625,019, Relyveld, there is described the crosslinking agent of daunorubicin with glutaraldehyde to form a water insoluble polymeric complex wherein the insoluble fraction upon resuspension in an aqueous medium in the absence of glutaraldehyde will gradually release the desired anti-tumor agent in a soluble form. This method consists mainly in mixing together daunorubicin, an antibody and glutaraldehyde, which can combine in three different ways. The conjugates obtained comprise the following mixture of polymeric products:

| | | |
|---|---|---|
| 1- 33% | Antibody - glutaraldehyde - Daunorubicin |
| 2- 33% | Antibody - glutaraldehyde - Antibody |
| 3- 33% | Daunorubicin - glutaraldehyde - Daunorubicin | wherein only the antibody-glutaraldehyde-daunorubicin conjugate is active. Furthermore, these three possible conjugates can be linked together by the excess glutaraldehyde in solution to form an agglomerate, which makes it difficult to isolate the active conjugate which is an autopolymerized anti-tumor agent.

This method is not readily reproducible and gives an unstable conjugate product. Unfortunately, this autopolymerized anti-tumor agent has the disadvantage of being insoluble in water and thus loses its specific activity against tumor cells. This insoluble product cannot be used intravenously for a systemic treatment since it is taken up by phagocytic cell such as monocytes, macrophages or cells. Finally, this product is not very stable and therefore does not have a very long shelf life.

Shen and Ryser (Biochem. Biophys. Res. Commun., 1981, 102, 1048) have reported the use of maleic anhydride (A) and cis aconitic anhydride (B) for the conjugation of daunorubicin on solid supports or proteins.

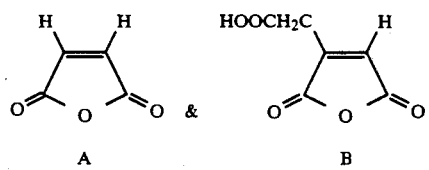

These adducts do not have any pharmacological activity, since they release the drug at a pH of 4.0. The drug remains attached to these coupling agents at the physiological pH of 7.4.

It would therefore be highly desirable to have a conjugation agent which provides highly stable anti-tumor-conjugation agent-protein complexes which could release the drug at the targeted site under adequate physiological conditions. It would be also desirable, if such a product was stable at room temperature for a long period of time without having polymerization problems, and if such compounds could be handled by anyone having minimal knowledge of this subject matter instead of specialized personnel. It is also highly desirable that such conjugation agent decreases the toxicity of the drug while enhancing its effectiveness.

Furthermore, it would be of a great advantage if there could be provided intermediates of such compounds which would be stable for months at room temperature.

SUMMARY OF THE INVENTION

Surprisingly and in accordance with the present invention, there is provided a new conjugation agent for coupling anti-tumor agents with different protein carriers for enchanced drug targeting. The novel conjugation agents of the present invention are maleic anhydride derivatives which are useful in forming conjugated compounds which have not only an increase of pharmacological activity and a decrease of toxicity, but are also highly stable at room temperature without any fear of polymerization due to air oxidation.

In accordance with the present invention, there is provided new conjugated compounds of the general formula I:

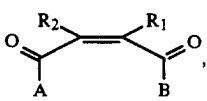

wherein,
R₁ and R₂ are each independently members selected from the group consisting of:
(1) hydrogen atom;
(2) phenyl;
(3) phenyl substituted by at least one member selected from the group consisting of hydroxy, halogen, lower alkyl, lower alkoxy or nitro;
(4) $C_{1-4}$ alkyl;
(5) $C_{1-4}$ alkoxy; and
(6) $C_{1-6}$ carboxyalkyl;
with the proviso that R₁ and R₂ cannot be simultaneously a hydrogen atom, and when one of R₁ or R₂ is a hydrogen atom, the other one cannot be —CH₂COOH;
A is the residue of an anti-tumor agent containing at least one amino group available to form an amide bound; and
B is a member selected from the group consisting of:
(1) hydroxy;
(2) a radical of the general formula II a

   IIa wherein,
X is O, S or Se; and
R₃ is member selected from the group consisting of:
(a) phenyl;
(b) phenyl substituted by at least one member selected from the group consisting of hydroxy, halogen, lower alkyl, lower alkoxy, nitro or cyano;
(c) SO₂-alkyl;
(d) azobenzene;
(e) azobenzene substituted by at least one member selected from the group consisting of hydroxy, halogen, lower alkyl, lower alkoxy, nitro or cyano;
(f) isoquinoline;
(g) piperidine;
(h) naphthalene;
(i) pyridine;
(j) keto pyridine;
(k) benzotriazole substituted by at least one member selected from the group consisting of hydroxy, halogen, lower alkyl, lower alkoxy, nitro or cyano;
(l) cyclic imides containing 5 to 10 atoms;
(m) cyclic imides containing 5 to 10 atoms substituted by at least one of hydroxy, halogen, lower alkyl, lower alkoxy, nitro, cyano, phenyl, phenyl substituted by at least one of hydroxy, halogen, lower alkyl, lower alkoxy, nitro or cyano;
(n) phthalimide;
(o) phthalimide substituted by at least one of hydroxy, halogen, lower alkyl, lower alkoxy, nitro or cyano;
(p) $C_{2-4}$ alkenyl;
(q) $C_{2-4}$ alkenyl substituted by at least one member selected from the group consisting of hydroxy, halogen, lower alkyl, lower alkoxy, phenyl, nitro or cyano; and

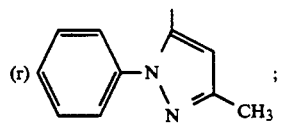

(3) a radical of the general formula II b

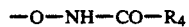   IIb wherein,
R₄ is a member selected from the group consisting of:
(a) lower alkyl;
(b) lower alkoxy;
(c) phenyl; and
(d) phenyl substituted by at least one of hydroxy, halogen, lower alkyl, lower alkoxy, nitro or cyano; and
(4) a residue containing a free ε-lysine selected from a peptide or a protein.

The conjugated compounds of the present invention are easily synthesized without any polymerization, since they are substantially pure. Furthermore, they are not oxidized in the presence of air, at room temperature, which means that their shelf life is extended significantly.

Other advantages of the present invention will be readily illustrated by referring to the following description.

IN THE DRAWINGS

FIG. 1 shows the cytotoxicity of a daunorubicin-bovine serum albumin conjugate prepared in accordance with the present invention using 2-methoxy-3-methyl maleic anhydride as the conjugation agent.

FIG. 2 shows the cytotoxicity of a daunorubicin-bovine serum albumin conjugate prepared in accordance with the present invention using 3-methoxy-2-phenyl maleic anhydride as the conjugation agent.

FIG. 3 shows the cytotoxicity of a daunorubicin-bovine serum albumin conjugate prepared in accordance with the present invention using 2-(3-carboxypropyl)maleic anhydride as a conjugation agent.

DETAILED DESCRIPTION OF THE INVENTION

The compounds of the present invention correspond to the general formula I:

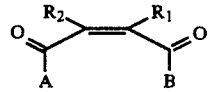   I wherein R₁, R₂, A and B are as defined previously.

As an example of an anti-tumor agent containing at least one amino group available to form an amide bound, there may be mentioned 5,12-anthracyclinediones such as daunorubicin, epirubicin and doxorubicin and 7-alkylamino mitomycin derivatives such as the one of general formula III described by Iyengar B.S. et al. (J. Med. Chem., 1986, 29, 1760; J. Med. Chem., 1983, 26, 16) which are listed below;

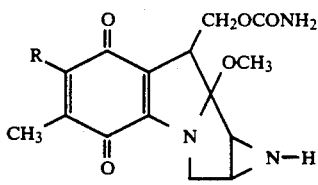

wherein,
R is selected from the group consisting of:
—NH(CH$_2$)$_2$NH$_2$;
—NH(CH$_2$)$_3$NH$_2$;
—NH(CH$_2$)$_2$SH;
—NH(CH$_2$)$_2$OH;
—NH(CH$_2$)$_2$O(CH$_2$)$_2$OH;
—NH(CH$_2$)$_2$O(CH$_2$)$_2$NH$_2$;
—NH(CH$_2$NH$_2$)$_2$;
—NH(CH$_2$)$_4$NH(=NH)CNH$_2$;
—NHCH$_2$(OH)CHCH$_2$NH$_2$; and
—NHCH$_2$(OH)CHCH$_2$OH.

As an example of suitable substituents falling within the scope of R$_3$, there may be mentioned nitrophenyl, pentachlorophenyl, pentafluorophenyl, 2,4,5-trichlorophenyl, -N-phthalimidyl, -N-succinimidyl and -N-piperidinyl.

Protein and Peptide

The proteins and peptides are only used in order to direct the conjugates to the desired cell line used or in order to maintain the drug in the blood circulation for a prolonged period of time.

This method is generally applicable to all proteins bearing in their structure one or more free ε-lysine residues, for example: erythrocytes, ghost, microvesicles, blood platelets and albumin derivatives. As preferred proteins there may be mentioned bovine serum albumin, human serum albumin, transferrin and some gamma globulins with success.

As proteins, there may also be used antibodies. The antibodies are obtained through standard monoclonal antibody production procedures using cell lines described herein. As an example of suitable antibodies, there may be mentioned: anti-carcinoembryonic, anti-alphafetoprotein, anti-embryonic pre-albumin and gastrin releasing peptide (GRP). As an example of suitable peptide, there may be mentioned lys-bombesin.

Cell Lines

The cell lines are only used to show that the conjugates of the present invention are still active. As cell lines there may be used: human embryonic intestine cells (CCL-6), human amnion cells (CCL-25), human osteosarcoma cells (CRL-1427), human ovarian carcinoma (CRL-1572), human hepatoma cells (HS-703-T), Mouse melanoma (CRL-6323) and LoVo human adenocarcinoma cells (CCL-229). These cell lines are readily available from the American Type Culture Collection under the numbers shown in brackets, except for the human hepatoma (HS-703-T) which can be obtained from Dr. Williams C. Parks at Michigan State University, East Lansing, Mich., U.S.A.

All cell lines are routinely cultured in RPMI-1640 ® medium supplemented with 10% fetal bovine serum and 100 μg per mL of streptomycin and 100 μg per mL of penicillin.

The conjugated compounds of formula I of the present invention are generally prepared as follows:

a—by reacting an anti-tumor agent with a compound of the general formula IV

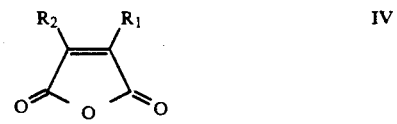

wherein R$_1$ and R$_2$ are as defined previously;

b—by purifying the A-conjugation agent complex by extraction with dichloromethane, and/or other suitable organic solvents in aqueous acidic solution; and c—reacting the dissolved A-conjugation agent complex in phosphate buffer solution with a desired protein carrier (B) and isolating the conjugated compounds from the reaction mixture.

The preparation of the compounds of the general formula IV of the present invention are illustrated in the following scheme:

Synthetic scheme of new conjugating agent

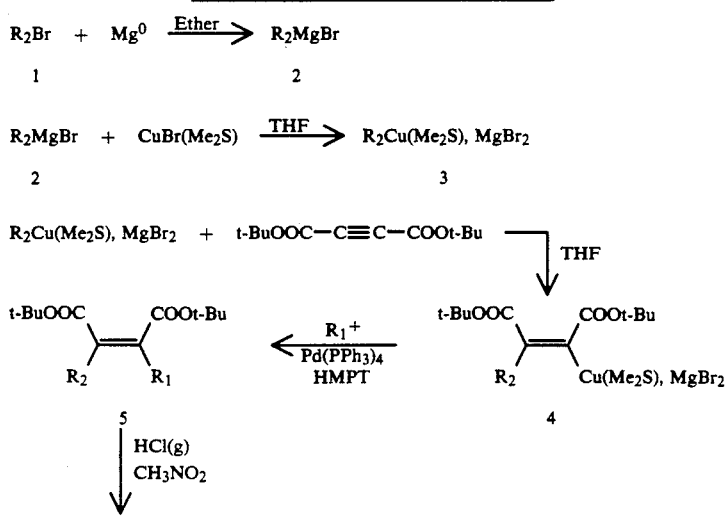

-continued

Synthetic scheme of new conjugating agent

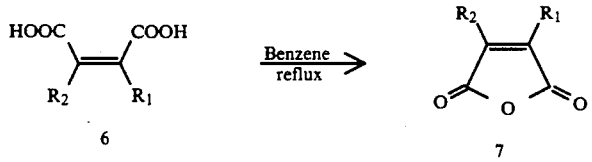

1. An $R_2Br$ 1 derivative wherein $R_2$ is other than hydrogen is reacted with $Mg°$ in anhydrous ether under dry argon atmosphere at room temperature for 15–30 minutes, then gently refluxed for 15–30 minutes to obtain the $R_2MgBr$ 2 derivative.

2. $R_2MgBr$ 2 derivative is reacted with a stoechiometric amount of copper bromide dimethyl sulfide complex at $-78°$ C. under dry argon atmosphere, leading to a yellow suspension of organocopper intermediate $R_2Cu(Me_2S)$, $MgBr_2$ 3.

3. To the yellow suspension of 3 is slowly added a stoechiometric amount of di-t-butyl acetylenedicarboxylate at $-78°$ C. The mixture is reacted for 12 hours at $-78°$ C. leading to complex

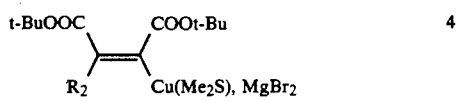

4. Complex 4 in anhydrous THF, and is hydrolysed by addition at $-78°$ C. of an aqueous solution saturated with ammonium chloride, the reaction proceeds in 12 hours to yield a 2-substituted maleic anhydride derivative. Various electrophiles can be used instead of ammonium chloride in order to yield 2,3-disubstituted maleic anhydride derivatives. In this case, the reactions are conducted at $-78°$ C. in presence of 2 molar equivalent of hexamethylphosphorous triamide (HMPT), a catalytic amount of tetrakis (triphenylphosphine) palladium ($Pd(PPh_3)_4$ and 1.6 equivalent of electrophile. After 12 hours, the mixture is hydrolysed at $-45°$ C. with ammonium chloride solution as described previously leading to the di-t-butyl ester of maleate 5.

5. Compound 5 is deprotected in nitromethane solution, previously saturated at $0°$ C. with gaseous HCl, and left at room temperature for 1 hour. After evaporation and usual acid-base work-up from ether solution, the mono or 2,3-disubstituted maleic acid derivative 6 is obtained.

6. Finally, compound 6 is dehydrated by refluxing in anhydrous benzene for 12 hours leading to the desired mono or 2,3-disubstituted anhydride 7.

Following the procedures of the present invention, the following compounds of formula IV have been obtained:

| $R^1$ | $R^2$ |
|---|---|
| hydrogen | $OCH_3$ |
| $CH_3$ | $OCH_3$ |
| phenyl | $OCH_3$ |
| p-$OCH_3$ phenyl | $OCH_3$ |
| hydrogen | $CH_2CH_3$ |
| hydrogen | $CH_2CH(CH_3)_2$ |
| hydrogen | $CH_2CH=CH_2$ |
| hydrogen | $(CH_2)_2COOH$ |
| $CH_2CH=CH_2$ | $CH_2CH(CH_3)_2$ |
| $CH_2CH=CH_2$ | $CH_2CH_2COOH$ |
| iodine | $CH_2CH_2COOH$ |

'In vitro' Cytotoxicity

In order to evaluate the efficiency of the compounds of formula I, the following procedure is used while other methods of 'in vitro' cytotoxicity can be used. Cytotoxicity assays are conducted on LoVo cells. This type of cells is chosen for its responsibility in many cases of cancer in North America.

Tumor cells are obtained from the American Type Culture Collection. The cells are suspended at a concentration of $2.5 \times 10^4$ cells/mL in a fresh culture media (RPMI-1640 ®) supplemented with 10% fetal calf serum).

The well plates are seeded with 100 μl of the cell suspension and incubated 24 hours at $37°$ C. in an humidified atmosphere containing 5% $CO_2$. One hundred μl of fresh culture media containing different quantitites of the drugs to be tested (10 to 2500 ng) are added. Each test is conducted in triplicate. The cells are further incubated for 3 more days at $37°$ C. (humidified atmosphere, 5% $CO_2$). Cell survival is determined by MTT method (Denizot, F. et al., J. Immunol. Methods (1986), 89, 271; Pagé, M. et al., Int. J. Immunopharm. (1988), 10, 785). The method mainly consisted of a first removal of the culture media and addition to the plates of 20 μl of a MTT solution (5 mg/mL in PBS pH 7.4). The plates are incubated at $37°$ C. for 4 hours and then 200 μl of dimethylsulfoxide is added into the wells. The plates are agitated for 15 min at room temperature and the absorbance at 540 nm measured on Titertek MC Multiwell ® spectrophometer.

The method normally used by the American National Cancer Institute for the comparison between drugs is based upon $ID_{50}$, being the concentration at which half of tumor cell population is killed. A comparison of the anti-tumor agent-protein conjugates of the present invention of general formula I (A=daunorubicin (DNR), B=bovine serum albumin (BSA), $R_1$ and $R_2$ are as defined previously) are compared to daunorubicin alone, to their DNR-conjugation agent intermediate of general formula I (A=DNR, B=hydroxy) and to the BSA-cis aconityl-DNR modified conjugate of general formula I of Shen and Ryser (A=DNR, B=BSA, $R_1$=H and $R_2$=$CH_2COOH$) at physiological conditions (pH=7.4). The actual Shen and Ryser conjugate wherein A=DNR, B=aminoethyl polyacrylamide (sold as Affi-gel 701 ® by Bio-Rad, California, USA) $R_1$ and $R_2$=H or $R_1$=H while $R_2$=$CH_2COOH$ are highly insoluble in aqueous mixtures such as blood, plasma, etc. To test the activity of these conjugates, Shen and Ryser have preincubated their conjugates in buffered aqueous solutions at pH<6 for 18 hours at $37°$ C., centrifuged the mixture to remove the insoluble aminoethyl polyacrylamide polymer and tested the supernatant containing the free DNR on tumor cells. Such procedure is useless for 'in vitro' and 'in vivo' usage of anti-tumor agent conjugates. Thus, we have modified B for BSA instead of aminoethyl polyacrylamide in order to obtain a water soluble conjugate compatible with experiments in living systems such as tumor cell cultures.

The method of the present invention for coupling an anti-tumor agent to a protein provides molar ratios of anti-tumor to protein varying from 1 to 12 as desired. The preferred molar ratios for coupling anti-tumor agent to protein being 2 to 6.

Results obtained using this new procedure show that the pharmacological activity of the drug can be saved while limiting the undesirable polymerization of the protein normally encountered with homobifunctional coupling agents. This procedure is simple, reproducible and most reagents are available commercially. The anti-tumor-conjugation agent complexe can be stored for months at room temperature.

The present invention will be more readily understood by referring to the following Examples which are given to illustrate the invention rather than to limit its scope.

EXAMPLE I

Preparation of 2-methoxy-3-methyl maleic anhydride (according to the procedure of Kaiser et al., *Can. J. Chem.*, 1986, 64, 104–109)

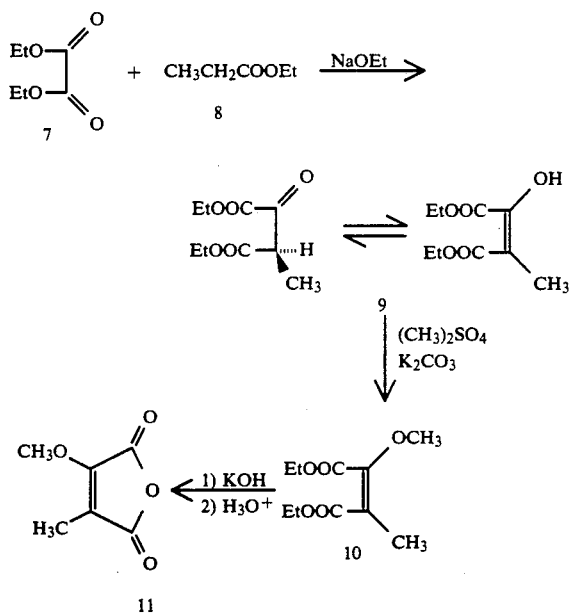

Diethyl 2-methyl oxaloacetate (9)

48.6 mL of ethyl oxalate 7 (0.36 mol) is added dropwise to a cooled (10° C.) solution of 20 mL of sodium ethanoate (0.38 mol, prepared 'in situ' by mixing 15.25 g of sodium anhydride (0.64 mol) in 20 mL of anhydrous ethanol and 200 mL of diethyl ether) and ethyl propionate 8 (36.5 mL, 0.32 mol). The mixture is then refluxed for 170 min., cooled in an ice bath and diluted with 150 mL of distilled water. The solution is acidified to pH 2-3 with HCl 6M and extracted with ether (3×125 mL). The organic extracts are combined, dried over $CaCl_2$, filtered and evaporated under reduced pressure.

The residue is distilled under vacuum giving compound 9 at a yield of 61%. B.P. 81°-85° C./3 mmHg, Litt. 75°-78° C./2 mmHg.

Diethyl (2-methoxy-3-methyl) oxaloacetate (10)

Under anhydrous conditions, compound 9 (8.1 g, 0.04 mol), and potassium carbonate (8 g, 0.057 mol) are mixed in 100 mL of anhydrous acetone. Four mL of dimethylsulfate (0.042 mol) is added dropwise to the mixture, then the mixture is brought to gentle reflux. The mixture is further refluxed for another 2 hours, then cooled in an ice bath, filtered and the solvent is evaporated. The remaining residue is distilled under vacuum, giving compound 10 at a yield of 67.8%. B.P. 96°-98° C./0.2 mmHg.

Preparation of 2-methoxy-3-methyl maleic anhydride (11)

In a round bottom flask, compound 10 (4.32 g, 0.020 mol) is dissolved in 25 mL of a 4M aqueous solution of KOH and refluxed for 2 hours. The cooled solution is acidified to pH 2 with HCl 6M and extracted with ether (5×30 mL). The organic extracts are combined, dried over anhydrous $MgSO_4$, filtered, and the solvent is evaporated under reduced pressure. The white solid obtained is recrystallized in benzene or ether.

There is obtained 2-methoxy-3-methyl maleic anhydride 11 at a yield of 71.4%. M.P. 41°-43° C. (Litt. 40°-42° C.), $^1$HNMR ($CDCl_3$) 2.013 ppm ($CH_3$), 4.238 ppm ($OCH_3$) IR (KBr) 1860, 1765, 1665 $cm^{-1}$.

EXAMPLE II

Preparation of 3-methoxy-2-phenyl maleic anhydride (according to the procedure of Kaiser et al., *Can. J. Chem.*, 1986, 64, 104–109)

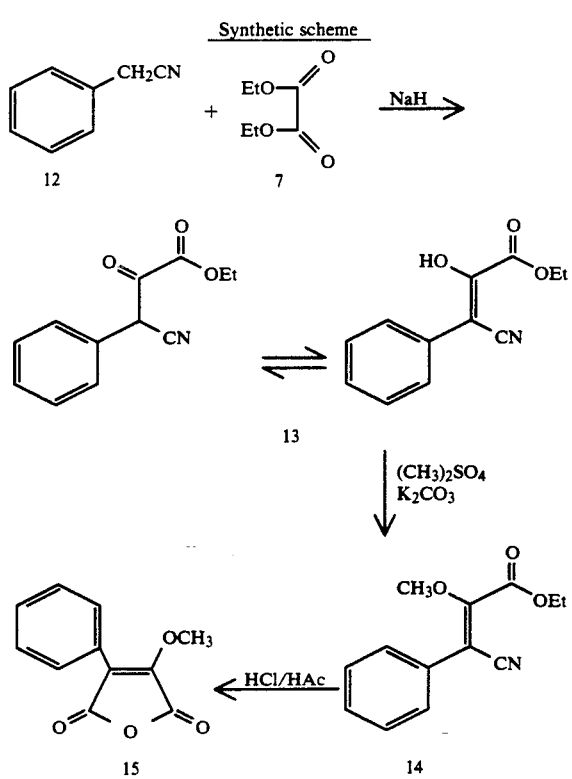

Ethyl 3-cyano, 3-phenyl pyruvate (13)

Under anhydrous conditions, a mixture of phenylacetonitrile 12 (8.1 g, 0.070 mol), diethyl oxalate 7 (27.9 mL, 0.20 mol), sodium hydride (5.2 g, 0.22 mol, suspended in 250 mL of dry ether) and 2 drops of anhydrous ethanol are refluxed for 19 hours. The mixture is cooled in an ice bath and the excess of hydride is destroyed by dropwise addition of ethanol. The salts produced during the destruction of hydride are solubilized by addition of distilled water. Organic phase is separated and the aqueous phase extracted with ether (3×100 mL). The aqueous phase is acidified to pH 2-3 with HCl 6M. Thus allowing a white solid to precipitate. The solid is washed with cold distilled water and recrystallized in benzene.

There is obtained the ethyl 3-cyano, 3-phenyl pyruvate 13 at a yield 82.9%. M.P. 130°-131° C. (Litt. 129°-130° C.) $^1$HNMR (CDCl$_3$) 1.49 ppm (t, 3H), 4.531 ppm (q, 2H), 7.352-7.426 ppm (m, 4H), 7.649-7.704 ppm (m, 2H) IR (neat) 3010, 2215, 1725, 1625 cm$^{-1}$.

Ethyl 2-methoxy, 3-cyano, cinnamate (14)

Under anhydrous and inert conditions is slowly added 4 mL of dimethylsulfate to a mixture of ethyl 3-cyano-3-phenyl pyruvate 13 (8.68 g, 0.04 mol) and potassium carbonate (8 g) in 100 mL of acetone. The mixture is refluxed for 2 hours. The subsequent work-up is identical to Example I.

There is obtained the ethyl 3-cyano-3-methoxy cinnamate 14. B.P. 128°-135° C./0.3 mmHg (Litt. 128° C./0.4 mmHg).

Preparation of 3-methoxy-2-phenyl maleic anhydride (15)

To a solution of compound 14 (5.78 g, 0.0025 mol) in acetic acid (62 mL) and distilled water (40 mL) is added, dropwise, sulfuric acid (52 mL, 12M) in order to maintain the temperature of the mixture below 105° C. throughout the addition. At the end of the addition, the solution is cooled in an ice bath, diluted with 150 mL of distilled water and extracted with ether (3×60 mL). Ether extracts are extensively washed with an aqueous solution of KOH 2M. The basic aqueous phase is then acidified at pH 2-3 with H$_2$SO$_4$ 6M and extracted again with ether (3×60 mL). The extracts are dried over anhydrous MgSO$_4$, the ether is evaporated under reduced pressure and the crude product recrystallized in methanol.

There is obtained 3-methoxy-2-phenyl maleic anhydride 15 at a yield of 77%. M.P. 113°-114° C. (Litt. 115°-116° C.) $^1$HNMR (CDCl$_3$) 4.381 ppm (s, 3H), 7.42 (m, 3H), 7.95 (m, 2H) IR (KBr) 1825, 1750, 1620, cm$^{-1}$.

Mass calculated: 204.0423
Mass obtained: 204.0426

EXAMPLE III

Preparation of 2-allyl maleic anhydride

Synthetic scheme

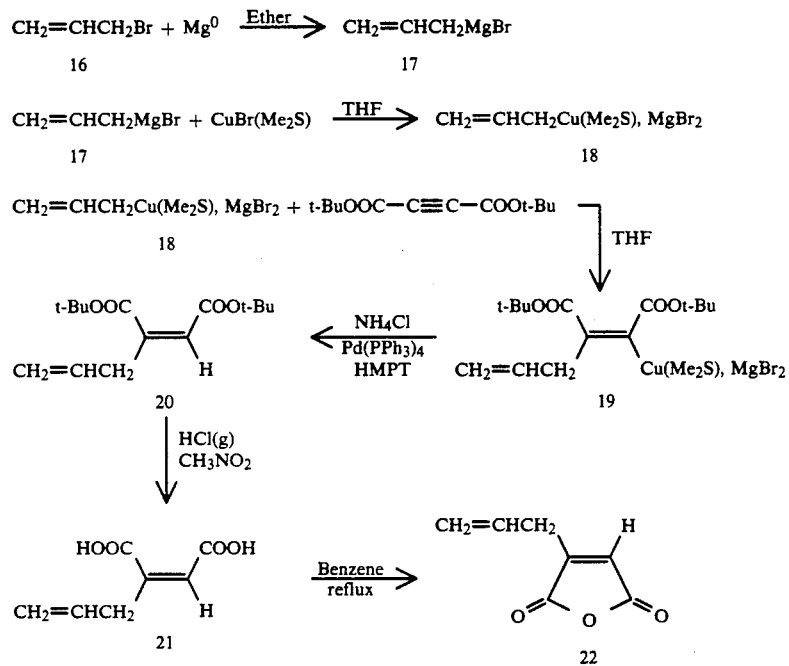

Preparation of allyl magnesium bromide (17)

Allyl bromide 16 (19 g, 0.157 mol) dissolved in 50 mL of anhydrous ether is slowly added to 4.36 g (0.18 mol) of metallic magnesium in order to maintain a gentle reflux. The reaction takes place under argon atmosphere and strictly anhydrous conditions. At the end of the addition, the reaction mixture is refluxed for 15-20 minutes allowing completion of the reaction. The mixture is cooled in an ice bath and the Grignard's reagent 17 in the mixture is quantitated according to Watson and Eastham (Watson, S.C., and Eastham, J. F., J. Organometal; Chem., 1967, 9, pp. 165-168).

There is obtained the allyl magnesium bromide 17.

Preparation of 2-allyl-di-t-butyl maleate (5)

A 1.88M solution of 17 (2.1 mL, 4.0 mmol) is added dropwise to a solution of cuprous bromide-dimethyl sulfide complex (0.82 mL, 4.0 mmol), in anhydrous tetrahydrofuran (5 mL) and dimethyl sulfide (4 mL)

under argon at −78° C. The resulting suspension 18 of a yellow solid is subsequently stirred for 2 hours at −78° C. and a solution of freshly distilled di-t-butyl acetylenedicarboxylate (0.91 g, 4.0 mmol) dissolved in anhydrous tetrahydroufuran (5 mL) is added over a period of 1 minute at the same temperature. The mixture is then stirred for 12 hours at −78° C. The reaction is then quenched with aqueous ammonium chloride at −78° C. and the mixture is allowed to slowly reach 0° C. After the usual work-up with ether, the product is isolated by dry column chromatography technique (Silica Gel G60, eluent=hexane: ethyl acetate 4:1).

There is obtained 2-allyl-di-t-butyl maleate 20 at a yield of 61%. $^1$HNMR (CDCl$_3$) 1.43 ppm (s, 9H), 1.47 ppm (s, 9H), 2.98 ppm (dd, 1H, H$_d$, J$_{dc}$=2.93 Hz, J$_{df}$=1.47 Hz), 3.01 ppm (dd, 1H, H$_e$, J$_{ec}$=2,74 Hz, J$_{ef}$=1.83 Hz), 5.08 ppm (q, 1H, H$_b$, J$_{bc}$=2.48 HZ), 5.15 ppm (q, 1H, H$_a$, J$_{ac}$=2.39 Hz), 5.67 ppm (t, 1H, Hf, J$_{df}$=1.47 Hz, J$_{fe}$=1.83 Hz), 5.74 ppm (m, 1H, H$_c$),

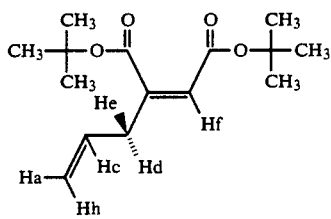

IR cm$^{-1}$ 3090, 2990–2940, 1725, 1660–1620, 1370 cm$^{-1}$.
Mass calculated: 268.1675
Mass obtained: 268.1641.

2-allyl maleic anhydride 22

2-allyl-di-t-butyl maleate 20 (0.59 g, 2.2 mmol) is dissolved in dry nitromethane (40 mL). The solution is cooled at 0° C. and saturated with gaseous dry HCl. Then the mixture is stirred for 1 hour at room temperature. Nitromethane is evaporated under reduced pressure, the residue dissolved in ether, washed with saturated NaHCO$_3$ aqueous solution (3×50 mL). The aqueous solutions are combined, acidified to pH 2 with HCl 6M, and extracted with ether (3×50 mL). The organic extracts are combined and dried over MgSO$_4$. After filtration, the ether is evaporated under reduced pressure the 2-allyl maleic acid 21 obtained is dissolved in anhydrous benzene (60 mL), then refluxed for 2 hours or until no more water appears in the Dean-Stark trap. Benzene is evaporated under reduced pressure and the residue distilled under vacuum.

There is obtained 2-allyl maleic anhydride 22 at a yield of 70%. B.P. 72°–74° C./3.5 mmHg, $^1$HNMR (CDCl$_3$), 3.22 ppm (d, 1H, H$_d$, J$_{df}$=1.83 hz) 3.25 ppm (d, 1H, H$_e$), 5.25 ppm (m, 2H, H$_a$ and H$_b$), 5.84 ppm (m, 1H, H$_c$) and 6.62 ppm (t, 1H, H$_f$, J$_{fd}$=1.83 Hz, J$_{fe}$=2.20)

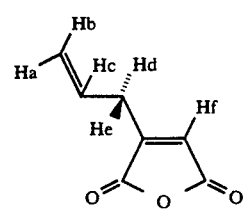

EXAMPLE IV

Preparation of 2-(3-carboxypropyl) maleic anhydride

Proceeding in the same manner as in Example III and replacing allyl bromide 16 by 2-(2-bromoethyl)-1,3-dioxolan, there is obtained compound 21a.

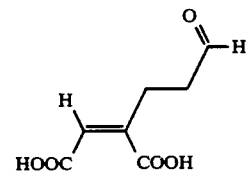

400 mg of compound 21a is dissolved in 50 ml of ether and a slow stream of oxygen is bubbled through the solution for 2 hours at room temperature. The solvent is evaporated, compound 21b is obtained.

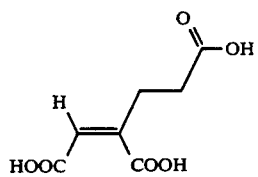

The dehydration of compound 21b is performed according to the procedure described in Example III. There is obtained 2-(3-carboxypropyl) maleic anhydride at a 50% yield, $^1$HNMR (CDCl$_3$) 3.30 ppm (t, 2H, J=4.02 Hz), 4.92 ppm (m, 2H), 6.61 ppm (t, 1H, J=1.83 Hz), 10.21 ppm (s, 1H, COOH).

EXAMPLE V

Synthetic scheme of daunorubicin "activation"

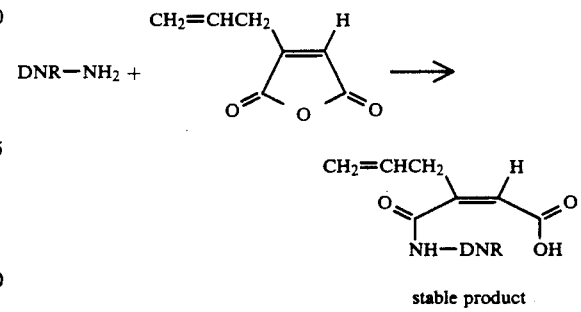

stable product

Preparation of 2-allyl, maleyl-daunorubicin derivative 12 mg of daunorubicin sold under the trademark Cerubidin ® (Rhône-Poulenc, Montreal, Canada) is dissolved in 4 mL of phosphate buffer (0.2M, pH 8). The solution is cooled to 0° C., energitically stirred solution and 4 portions of 2-allyl maleic anhydride are added slowly over a period of 180 min. It must be pointed out that the pH of the solution should be maintained at 8 throughout the reaction by addition of 1M NaOH, otherwise the yield of the reaction will dramatically decreased. After the addition, the mixture is extracted with dichloromethane (3×4 mL) in order to eliminate all unreacted daunorubicin. The pH of the aqueous solution is adjusted at 3.5 to 4 by controlled addition of HCl 1M with a pH meter. The maleyl-daunorubicin derivative is extracted with ethyl acetate or dichloromethane (3×5 mL). The organic extracts are combined, dried over anhydrous $Na_2SO_4$ and the solvent is evaporated under reduced pressure.

There is obtained 2-allyl,maleyl-daubnorubicin conjugate at a yield of 60–75% and its purity is checked by TLC, $CHCl_3$:MeOH:$H_2O$ (80:30:4), on Silica Gel $G_{60}$.

$R_f$ = daunorubicin = 0.3
$R_f$ = 2-allyl,maleyl-daunorubicin = 0.02

EXAMPLE VI

Preparation of maleyl-epirubicin conjugate

Proceeding in the same manner as in Example V and replacing daunorubicin by epirubicin, there is obtained 2-allyl,maleyl-epirubicin conjugate.

EXAMPLE VII

Preparation of maleyl-7-alkylamino mitomycin conjugate

Proceeding in the same manner as in Example V and replacing daunorubicin by 7-alkylamino-mitomycin, there is obtained 2-allyl,maleyl-7-alkylamino-mitomycin conjugate.

EXAMPLE VIII

Preparation of 2-methoxy-3-methyl maleyl-daunorubicin conjugate

Proceeding in the same manner as in Example V and replacing 2-allyl maleic anhydride by the compound of Example I (2-methoxy-3-methyl maleic anhydride), there is obtained 2-methoxy-3-methyl maleyl-daunorubicin conjugate.

$R_f$ = daunorubicin = 0.3
$R_f$ = 2-methoxy-3-methyl maleyl-daunorubicin = 0.05

EXAMPLE IX

Preparation of 3-methoxy-2-phenyl maleyl-daunorubicin conjugate

Proceeding in the same manner as in Example V and replacing 2-allyl maleic anhydride by the compound of Example II (3-methoxy-2-phenyl maleic anhydride), there is obtained 3-methoxy-2-phenyl maleyl-daunorubicin conjugate.

$R_f$ = daunorubicin = 0.3
$R_f$ = 3-methoxy-2-phenyl maleyl-daunorubicin = 0.03

EXAMPLE X

Preparation of 2-(3-carboxypropyl) maleyl-daunorubicin conjugate

Proceeding in the same manner as in Example V and replacing 2-allyl maleic anhydride by the compound of Example IV (2-(3-carboxypropyl) maleic anhydride), there is obtained 2-(3-carboxypropyl) maleyl-daunorubicin conjugate.

$R_f$ = daunorubicin = 0.3
$R_f$ = 2-(3-carboxypropyl) maleyl-daunorubicin = 0.01

EXAMPLE XI

Preparation of activated ester of maleyl-daunorubicin derivative

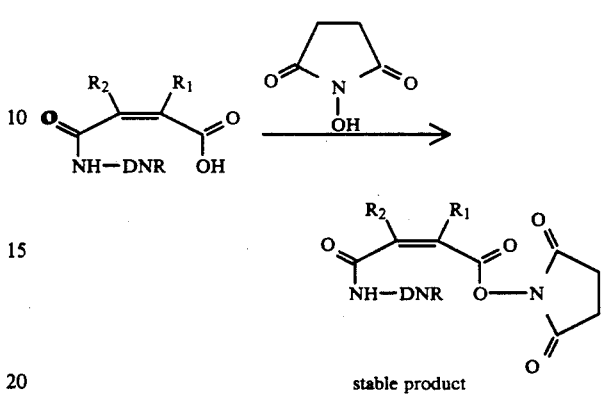

stable product

The preparation of activated esters with N-hydroxysuccinimide proceed generally through the following procedure:

To a cooled (0° C.) solution of maleyl-daunorubicin derivative dissolved in anhydrous tetrahydrofuran (THF, 2 mL), is slowly added, a cooled solution of dicyclohexylcarbodiimide (1 mg, $4.8 \times 10^{-6}$ mol in 1 mL of anhydrous THF) and a cooled solution of N-hydroxysuccinimide (2.2 mg, $19.2 \times 10^{-6}$ mol in 2 mL of THF). The reaction mixture is stirred at room temperature overnight. The mixture is then centrifuged in order to remove all dicyclohexylurea formed during the reaction. The solution is evaporated and the residue dissolved in a minimal amount of THF (about 0.5 mL) and precipitated by addition of dry 2-propanol (about 0.5 to 0.75 mL).

There is obtained maleyl-daunorubicin-N-hydroxysuccinimide conjugate at a yield of 60–65% (for cis aconityl derivative) and the compound has the following characteristics TLC, Silica Gel $G_{60}$, $CHCl_3$: MeOH: $H_2O$ (80:30:4) $R_f$: daunorubicin = 0.13, $R_f$: cis aconityl daunorubicin = 0.03; $R_f$: N-hydroxysuccinimidyl ester of cis aconityl daunorubicin = 0.71.

EXAMPLE XII

Conjugation of maleyl daunorubicin derivatives to proteins

To a solution containing maleyl-daunorubicin derivative ($5 \times 10^{-7}$ mol) and 10 mg of the desired protein in a 5 mM phosphate buffer solution (2 mL, pH 7.4) is added 1-(3-dimethylaminopropyl) 3-ethyl carbodiimide hydrochloride ($1.13 \times 10^{-4}$ mol). The solution is incubated at 37° C. for 2 hours. The protein-daunorubicin conjugate is then purified by chromatography on Sephadex-G25 ® (PD-10). The conjugate is sterilized by filtration over a Nuclepore filter (0.22 μm).

There is obtained maleyl-daunorubicin-protein conjugate. Conjugation ratio of 2:1 in relation to the protein is generally observed.

EXAMPLE XIII

Conjugation of 2-methoxy-3-methyl maleyl-daunorubicin conjugate to proteins

Proceeding in the same manner as in Example XI and replacing maleyl-daunorubicin derivative by the compound of Example VII (2-methoxy-3-methyl maleyl-daunorubicin) and wherein the desired protein is bovine serum albumin (BSA), there is obtained daunorubicin (DNR)-2-methoxy-3-methyl maleyl-BSA conjugate. The effect on LoVo cells of this DNR-BSA conjugate is shown in FIG. 2. The pharmacological activity of this DNR-BSA is slightly lowered than DNR alone ($ID_{50}$ of daunorubicin = 100 nM compared to 300 nM with DNR-2-methoxy-3-methyl maleyl-BSA). It is important to point out that the evaluation of the cytotoxic activity of a drug is mainly based on its $ID_{50}$ which mean: quantity of drug needed to kill 50% of the cell population concern by the study. Furthermore, the cytotoxicity of this new conjugate is much more important than with conjugates with maleic and cis aconitic anhydride previously experimented by Shen and Ryser ($ID_{50}$ of DNR-cis aconitic-BSA = >9000 nM and $ID_{50}$ of DNR-2-methoxy-3-methyl maleyl-BSA is 300 nM, which is 30 times more potent than the conjugate already reported by Shen and Ryser).

EXAMPLE XIV

Conjugation of 3-methoxy-2-phenyl maleyl-daunorubicin conjugate to proteins

Proceeding in the same manner as in Example XI and replacing maleyl-daunorubicin derivative by the compound of Example VIII (3-methoxy-2-phenyl maleyl-daunorubicin) and wherein the desired protein is bovine serum albumin (BSA), there is obtained daunorubicin (DNR)-3-methoxy-2-phenyl maleyl-BSA conjugate. The effect on LoVo cells of this DNR-BSA conjugate is shown in FIG. 1. The pharmacological activity of this DNR-BSA is slightly lowered than DNR alone ($ID_{50}$ of daunorubicin = 100 nM compared to 700 nM with DNR-3-methoxy-2-phenyl maleyl-BSA). It is important to point out that the evaluation of the cytotoxic activity of a drug is mainly based on its $ID_{50}$ which mean: quantity of drug needed to kill 50% of the cell population concern by the study. Furthermore, the cytotoxicity of this new conjugate is much more important than with conjugates with maleic and cis aconitic anhydride previously experimented by Shen and Ryser ($ID_{50}$ of DNR-cis aconitic-BSA = >9000 nM and $ID_{50}$ of DNR-2-methoxy-3-methyl maleyl-BSA is 700 nM, which is 10 times more potent than the conjugate already reported by Shen and Ryser).

EXAMPLE XV

Conjugation of 2-(3-carboxypropyl) maleyl-daunorubicin conjugate to proteins

Proceeding in the same manner as in Example XI and replacing maleyl-daunorubicin derivative by the compound of Example X (2-(3-carboxypropyl) maleyl-daunorubicin) and wherein the desired protein is bovine serum albumin (BSA), there is obtained daunorubicin (DNR)-2-(3-carboxypropyl) maleyl-BSA conjugate. The effect on LoVo cells of this DNR-BSA conjugate is shown in FIG. 3. The pharmacological activity of this DNR-BSA is slightly lowered than DNR alone ($ID_{50}$ of daunorubicin = 100 nM compared to 450 nM with DNR-2-(3-carboxypropyl) maleyl-BSA). It is important to point out that the evaluation of the cytotoxic activity of a drug is mainly based on its $ID_{50}$ which mean: quantity of drug needed to kill 50% of the cell population concern by the study. Furthermore, the cytotoxicity of this new conjugate is much more important than with conjugates with maleic and cis aconitic anhydride previously experimented by Shen and Ryser ($ID_{50}$ of DNR-cis aconitic-BSA = >9000 nM and $ID_{50}$ of DNR-2-methoxy-3-methyl maleyl-BSA is 450 nM, which is 20 times more potent than the conjugate already reported by Shen and Ryser).

EXAMPLE XVI

Conjugation of ester derivative of maleyl-daunorubicin derivatives to proteins

Proceeding in the same manner as in Example XI and replacing maleyl-daunorubicin derivative by the ester derivative of maleyl-daunorubicin and by omitting 1-(3-dimethylaminopropyl)-3-ethyl carbodiimide hydrochloride, there is obtained maleyldaunorubicin-protein conjugate.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known and customary practice within the art to which the invention pertains and as may be applied to the essential features hereinbefore set forth, and as follows in the scope of the appended claims.

I claim:

1. Compounds of the general formula I:

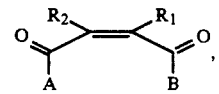

wherein,
R$_1$ and R$_2$ are each independently members selected from the group consisting of:
(1) hydrogen;
(2) phenyl;
(3) phenyl substituted by at least one member selected from the group consisting of hydroxy, halogen, lower alkyl, lower alkoxy or nitro;
(4) $C_1$-$C_4$ alkyl;
(5) $C_{1-4}$ alkoxy; and
(6) $C_{1-6}$ carboxyalkyl;
with the proviso that:
(1) when one of R$_1$ or R$_2$ is $C_{1-4}$ alkyl, then the other is not H or $C_{1-4}$ alkyl;
(2) R$_1$ and R$_2$ cannot be simultaneously hydrogen; and
(3) when one of R$_1$ or R$_2$ is H, then the other is not —CH$_2$COOH;

A is the residue of an anti-tumor agent containing at least one amino group available to form an amide bond; and B is a residue containing a free ε-lysine selected from a peptide or a protein.

2. Compounds according to claim 1, wherein said anti-tumor agent is selected from 5,12 anthracyclinediones and 7-alkylamino mitomycin derivatives.

3. A compound according to claim 1, the daunorubicin-2-methoxy-3-methyl maleyl-bovine serum albumin conjugate.

4. A compound according to claim 1, the daunorubicin-3-methoxy-2-phenyl maleyl-bovine serum albumin conjugate.

5. A compound according to claim 1, the daunorubicin-2-(3-carboxypropyl) maleyl-bovine serum albumin conjugate.

6. A method for treating cancer which comprises administering to a host a therapeutic dosage of a compound of formula I according to claim 1 wherein B is a protein or a peptide residue.

* * * * *